United States Patent [19]
Lichtenstein et al.

[11] Patent Number: 5,593,441
[45] Date of Patent: Jan. 14, 1997

[54] METHOD FOR LIMITING THE INCIDENCE OF POSTOPERATIVE ADHESIONS

[75] Inventors: Irving L. Lichtenstein, Marina Del Rey, Calif.; Carl R. Turnquist, Concord, Mass.; Parviz K. Amid, Calabasas, Calif.

[73] Assignee: C. R. Bard, Inc., Murray Hill, N.J.

[21] Appl. No.: 472,261

[22] Filed: Jun. 7, 1995

Related U.S. Application Data

[63] Continuation of Ser. No. 376,735, Jan. 23, 1995, abandoned, which is a continuation of Ser. No. 846,131, Mar. 4, 1992, abandoned.

[51] Int. Cl.⁶ .................................................. A61F 2/02
[52] U.S. Cl. ............................ 623/11; 600/37; 623/66; 606/151; 606/213
[58] Field of Search ........................... 623/11, 16, 66; 600/151, 213, 215, 37

[56] References Cited

U.S. PATENT DOCUMENTS

| | | |
|---|---|---|
| 4,400,833 | 8/1983 | Kurland .................................. 623/13 |
| 4,585,458 | 4/1986 | Kurland . |
| 4,713,075 | 12/1987 | Kurland . |
| 5,147,401 | 9/1992 | Bakker et al. ........................ 623/15 |
| 5,254,133 | 10/1993 | Seid ...................................... 606/213 |
| 5,258,000 | 11/1993 | Gianturco ............................. 606/151 |
| 5,282,851 | 2/1994 | Jacob-LaBarre ..................... 623/6 |
| 5,292,328 | 3/1994 | Hain et al. . |
| 5,433,996 | 7/1995 | Kranzler et al. . |

*Primary Examiner*—Paul B. Prebilic
*Attorney, Agent, or Firm*—Wolf, Greenfield & Sacks, P.C.

[57] ABSTRACT

A composite prosthesis and method for limiting the incidence of postoperative adhesions. The composite includes a mesh fabric and a barrier which prevents exposure of the mesh fabric to areas of potential adhesion. The interstices of the mesh fabric are infiltrated by tissue which secures the prosthesis in place. The composite is positioned with the barrier relative to the region of potential adhesion, such as the abdominal viscera.

5 Claims, 3 Drawing Sheets

METHOD FOR LIMITING THE INCIDENCE
OF POSTOPERATIVE ADHESIONS

This application is a continuation of Ser. No. 08/376,735, filed Jan. 23, 1995, now abandoned which is a continuation of Ser. No. 07/846,131, filed Mar. 4, 1992, now abandoned.

FIELD OF INVENTION

The present invention relates to an implantable composite prosthesis and method for limiting the incidence of postoperative adhesions.

BACKGROUND OF THE INVENTION

Various prosthetic mesh materials have been proposed to reinforce the abdominal wall and to close abdominal wall defects. In certain procedures, including incisional and umbilical hernia repair and chest reconstruction, the prosthetic mesh may come into direct contact with the sensitive abdominal viscera. Postoperative adhesions between the mesh and the intestine may occur, potentially leading to intestinal fistulization.

Various approaches to reducing the incidence of postoperative adhesions arising from the use of prosthetic mesh materials have been proposed by the prior art. It has been suggested to cover the prosthesis with peritoneum or other tissue, where available or adequate to close the defect, to form a biological barrier between the implant and the bowel. Also proposed has been the placement of a physical barrier between the surgical site and the surrounding tissue where adhesions are most commonly encountered.

U.S. Pat. No. 5,002,551 discloses a physical barrier formed of a knitted oxidized regenerated cellulose (Intercede(TC7)). The patent indicates that other physical barriers include silicone elastomers and absorbable gelatin films. Clinical studies of Interceed(TC7) were reported in "Prevention of Postsurgical Adhesions by Interceed(TC7), An Absorbable Adhesion Barrier: A Prospective, Randomized Multicenter Clinical Study", Fertility and Sterility, Vol. 51, No. 6, June 1989, pg. 93–938. Such physical barriers alone are not sufficient to reinforce the abdominal wall or to repair abdominal wall defects.

Jenkins et al., "A Comparison of Prosthetic Materials Used to Repair Abdominal Wall Defects", Surgery, Vol. 94, No. 2, August 1983, pg. 392–398, describes a technique of placing an absorbable gelatin film (Gelfilm®) freely between a piece of Marlex® knitted polypropylene monofilament mesh and the abdominal viscera. The gelatin film dissolved after one week. Thereafter, the incidence of adhesions was reported to be the same as with using the Marlex mesh alone.

Accordingly, the prior art lacks a prosthesis suitable for abdominal wall reconstruction and ventral hernia repair which combines the strength and pliability of a prosthetic mesh with the low incidence of postsurgical adhesions of a physical barrier.

SUMMARY OF THE INVENTION

The present invention is a composite prosthesis and method for reinforcing and repairing a weakened muscular wall while limiting the incidence of postoperative adhesions. The composite is formed of a biologically compatible, flexible and porous implantable material suitable for reinforcing tissue and closing tissue defects, particularly in the abdominal cavity, and a barrier for physically isolating the reinforcing material from areas likely to form adhesions, such as the abdominal viscera. The barrier and implantable material are permanently attached by an adhesive, stitching or insert molding in a manner which preserves sufficient openings in the material for tissue ingrowth.

In one embodiment of the invention, the composite includes attached sheets of knitted polypropylene monofilament mesh fabric and a silicone elastomer. The silicone elastomer is joined to the mesh by an adhesive which encapsulates the yarns of the mesh and bonds to the silicone elastomer. Regular points of attachment between the mesh fabric and the silicone elastomer sheeting provide a strong, integral composite prosthesis.

In another embodiment of the invention, the knitted polypropylene monofilament mesh fabric and silicone elastomer sheeting are sewn together with a polypropylene monofilament yarn. The knots are located on the mesh side of the prosthesis to minimize the exposure of the monofilament yarn to the areas of potential adhesion.

In a further embodiment of the invention, the silicone elastomer is insert molded to the mesh. The impregnation of the mesh by the molded silicone elastomer is limited to preserve sufficient openings in the mesh for tissue infiltration.

It is among the general objects of the invention to provide a prosthesis which combines the attributes of a surgical mesh fabric and of a physical barrier.

It is a further object of the invention to provide a prosthesis for repairing ventral hernias and for reconstructing the chest wall which limits the incidence of postoperative adhesions and intestinal fistulization.

It is a further object of the invention to provide a prosthesis which stimulates tissue infiltration without causing a similar inflammatory response of the abdominal viscera.

It is a further object of the invention to provide a prosthesis which may be custom shaped, sized and affixed during surgery without destroying the integrity of the device.

An additional object of the invention is to provide a prosthesis which is sufficiently flexible to conform to the surgical site.

Other objects and features of the present invention will become apparent from the following detailed description when taken in connection with the accompanying drawings which disclose multiple embodiments of the invention. It is to be understood that the drawings are designed for the purpose of illustration only and are not intended as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENTS

Figure 1A:
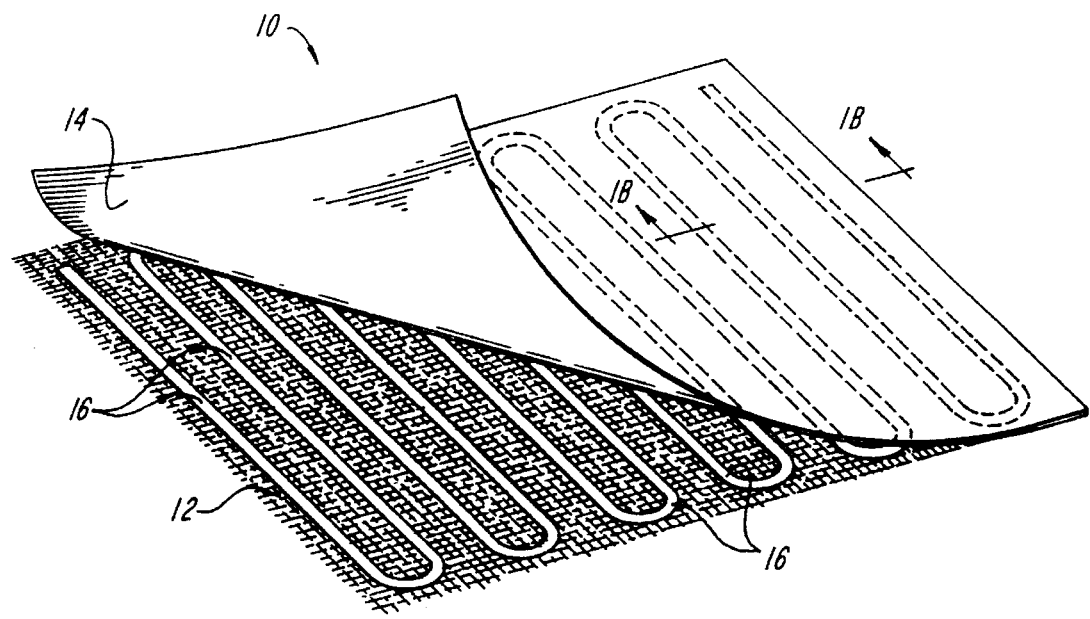
FIG. 1(a) is an illustration of the implantable composite prosthesis according to the present invention showing the serpentine pattern of adhesive.
Figure 1B:
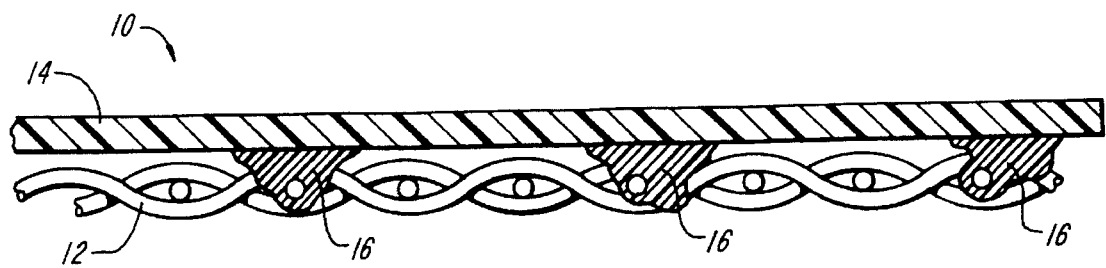
FIG. 1(b) is a sectional illustration along line 1(b) of FIG. 1(a)

The composite prosthesis 10 for limiting the incidence of postoperative adhesions shown in FIGS. 1(a)–(b) includes a tissue infiltratable fabric 12 and an adhesion barrier 14. The fabric is formed of a material which stimulates an inflammatory reaction in tissue after implantation and includes a plurality of openings which allow sufficient tissue ingrowth to secure the composite to host tissue. The barrier separates the fabric from the area of potential tissue adhesion. In the repair of ventral hernias and in chest wall reconstruction, the barrier isolates the abdominal viscera from the fabric, preventing intestinal adhesion and fistulization which may result from an inflammatory reaction of the bowel and the prosthetic mesh. The composite combines the strength, handling and fibroblastic stimulation of a prosthetic mesh with the low adhesion incidence of a physical barrier.

The relatively flat composite prosthesis sheet is sufficiently pliable to allow the surgeon to manipulate the shape of the implant to conform to the anatomical site of interest and to be sutured or stapled there. Alternatively, the composite may be pre-formed into a more complex shape, such as a tapered plug for filling and occluding a ruptured wall. The barrier need only cover that portion of the implant which is likely to be exposed to the intestine. The shape and size of the composite implant, and of the respective fabric and barrier, may vary according to the surgical application as would be apparent to those of skill in the art.

The tissue infiltratable fabric 12 includes a plurality of interstices or pores which are of sufficient size and orientation to allow tissue ingrowth. The barrier 14 is connected to the fabric 12 without detrimentally limiting the tissue infiltration. The barrier 14 preferably is formed of a translucent material which allows the physician to observe the location and integrity of the composite prosthesis during implantation. Holes may be formed through the barrier 14 to facilitate passage of neutrophiclic graneulocytes, reducing the incidence of infection. The holes should have dimensions sufficient to permit neutrophilic graneulocytic transport without detrimentally affecting the adhesion resistance of the composite.

The mesh fabric 12 and barrier 14 are integrally connected by an adhesive layer 16. A preferable serpentine pattern of adhesive is illustrated in FIG. 1 which provides a high density of points of attachment between the cover 14 and fabric 12 while still maintaining a sufficient quantity of open or non-impregnated interstices for tissue infiltration. The serpentine pattern maintains composite integrity by preventing the barrier and underlying fabric from separating if the prosthesis is custom cut by the surgeon to match a particular anatomical site.

Figure 2A:
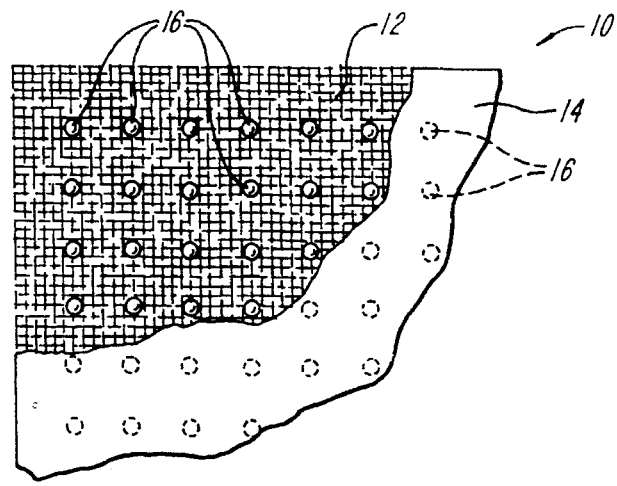
FIG. 2(a)–(b) are illustrations of adhesive patterns for joining the mesh fabric and the barrier sheeting.
Figure 2B:
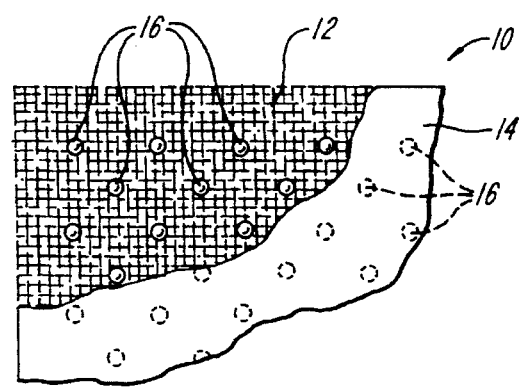

Alternatively, the adhesive may be applied in a grid-like pattern of dots or beads. In a representative arrangement, one and a half millimeter diameter dots with one centimeter uniform spacing form an effective joint between the fabric and the barrier. A pattern of uniformly spaced beads is shown in FIG. 2(a). A staggered configuration is shown in FIG. 2(b). Various other shapes, sizes and patterns of adhesive may be used as would be apparent to those of skill in the art.

The fabric 12 preferably is formed of a sheet of knitted polypropylene monofilament mesh fabric such as Marlex® mesh available from C. R. Bard, Inc. When implanted, the polypropylene mesh stimulates an inflammatory reaction which promotes rapid tissue ingrowth into and around the mesh structure. Alternatively, other surgical materials which are suitable for tissue reinforcement and defect closure may be utilized including Prolene®, Dacron®, Teflon® and Merselene®. Absorbable meshes, including polyglactin (Vicryl®) and polyglycolic acid (Dexon®), may be suitable for applications involving temporary repair of fascial defects. It also is contemplated that the mesh fabric may be formed from multifilament yarns and that woven, molded and other recognized methods of forming prosthetic mesh materials would be suitable.

The barrier 14 preferably is formed from a sheet of silicone elastomer such as Silastic® Rx Medical Grade Sheeting (Platinum Cured) distributed by Dow Corning Corporation. Silastic® does not substantially stimulate adhesion formation when implanted in tissue and is significantly less likely to cause an inflammatory reaction with neighboring tissue than would a prosthetic mesh. The silicone elastomer sheeting may be reinforced with Dacron® or other reinforcing materials. Other adhesion resistant materials also may be used as would be apparent to those of skill in the art. It is contemplated that Teflon® mesh, microporous polypropylene sheeting (Celgard®), expanded PTFE (Gorerex®) and oxidized, regenerated cellulose (Intercede(TC7)) alternatively may be used as barriers to adhesion and erosion. However, a composite formed of Intercede(TC7) may have only short term effectiveness, the Intercede(TC7) barrier being absorbed only a short period after implantation.

A preferred adhesive 16 for joining the silicone elastomer barrier to the knitted monofilament polypropylene mesh fabric is Silastic® Medical Adhesive Type A available from Dow Corning Corporation. The Silastic Medical Adhesive Type A forms a matrix which encapsulates the knitted polypropylene monofilament mesh fabric and bonds to the silicone elastomer sheet. Other adhesives may be utilized as would be apparent to those of skill in the art, the ultimate selection depending upon the composition of the fabric and the barrier.

A preferred procedure for applying the adhesive involves securing overlayed sheets of Marlex® knitted polypropylene monofilament mesh fabric and Silastic® silicone elastomer in a embroidery type hoop frame which includes an inner hoop, a variable diameter outer hoop and a hoop tightening mechanism. The Marlex® mesh and Silastic® sheets are pulled away from the hoops until sufficiently taut. It may be advantageous to stretch the mesh first and then the sheet of silicone elastomer to prevent pucking or wrinkling of the materials.

The frame is then secured on a positioning table of a liquid dispensing apparatus, such as the CAM/ALOT Model 1414 available from Camelot Systems, Inc. of Haverhill, Mass., with the mesh side facing the adhesive applicator. The adhesive is deposited under appropriate temperature and pressure through an appropriately sized needle positioned against the mesh surface so that the adhesive passes into the mesh interstices and against the bottom face of the silicone elastomer barrier. The deposition of the adhesive is computer controlled allowing the adhesive pattern (serpentine, spaced dots, etc.) to be pre-programmed.

In a representative embodiment, the composite includes a 10 inch by 14 inch sheet of Marlex® mesh knit from Marlex® polypropylene monofilament with a 0.006 inch diameter. A similarly sized 0.005 inch thick sheet of vulcanized silicone elastomer (Silastic®) is attached to the mesh with a serpentine pattern of 0.125 inch wide beads of adhesive (Silastic® Medical Adhesive A).

Figure 3:
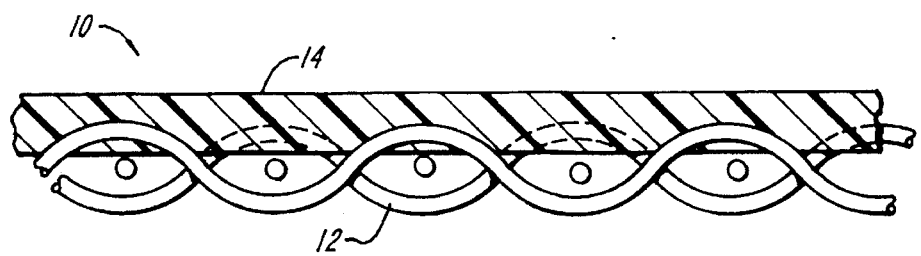
FIG. 3 is a sectional illustration of an insert molded implantable composite prosthesis according to the present invention.

A molded composite prosthesis 30 is illustrated in FIG. 3 and includes a prosthetic mesh substrate 32 which has been insert molded to a silicone elastomer barrier 34. The silicone elastomer does not completely impregnate the mesh interstices, preserving sufficient openings for tissue infiltration. Holes 36, which may be formed by upstanding pins in the mold, extend completely through the silicone elastomer barrier to provide a pathway for bacteria. The mesh fabric may be surface treated with a carbon dioxide plasma etch prior to molding which may enhance the union of the mesh and the silicone elastomer.

In a representative procedure, a Silastic® Q7-2213 Implant Grade Dispersion available from Dow Corning Corporation was poured into a mold with excess material being removed with a wooden spatula. A sheet of Marlex® mesh fabric was pressed into the mold until the pins impinged the knitted mesh. The solvent was evaporated in a chemical hood and then the dispersion was cured for one hour at 120° C.

Figure 4:
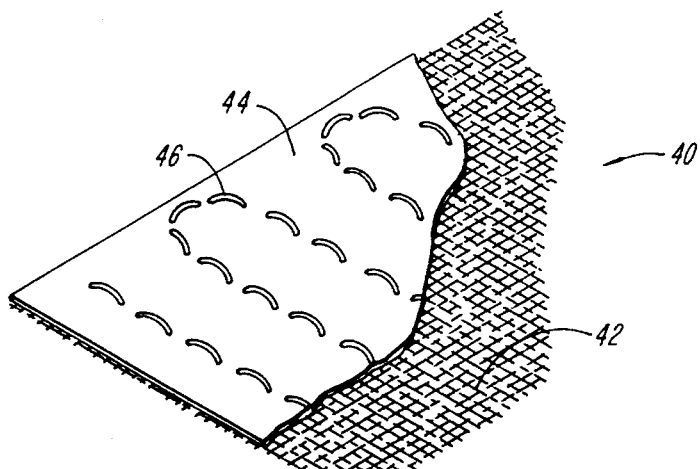
FIG. 4 is an illustration of a stitched implantable composite prosthesis according to the present invention.
Figure 5A:
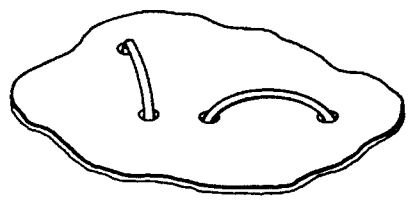
FIG. 5 is an illustration of a "blind hem stitch" for assembling the implantable composite prosthesis shown in FIG. 4.
Figure 5B:
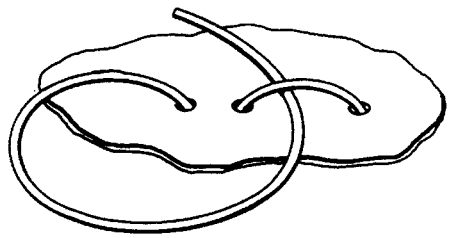
Figure 5C:
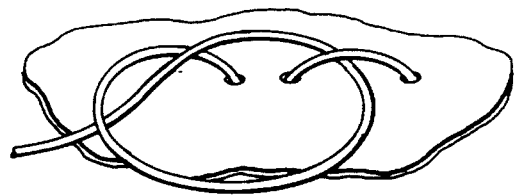

A stitched composite prosthesis 40 is illustrated in FIG. 4 and includes sheets of knitted polypropylene monofilament mesh fabric 42 and of a silicone elastomer 44 which are sewn together with a monofilament polypropylene yarn 46. The preferable stitching pattern ("blind hem stitch") illustrated in FIG. 5 ensures that the knots are formed on the mesh fabric side of the composite rather than on the elastomer side where they may cause localized adhesions with the bowel. In a representative embodiment, 0.5 to 1.0 centimeters long "blind hem" stitches were formed with a 0.006 inch diameter polypropylene monofilament and spaced every 0.5 to 1.0 centimeters, with seams spaced every 0.5 to 1.0 centimeters. A frame consisting of a flat bottom plate and a flat top plate with matching rectangular windows was used to hold the sheets of mesh and silicone elastomer during the sewing procedure.

A comparison of the composite prosthesis and a prosthesis consisting of Marlex® mesh alone has been made in rabbit and rat studies.

In the rabbit study, 4 cm×6 cm defects were created on each side of the abdominal wall muscle and peritoneum. The defects were patched by intraperitoneal placement in each rabbit of respective 5 cm×7 cm pieces of Marlex mesh and a composite prosthesis (opposing flat pieces of Marlex® mesh fabric and Silastic® joined by stitching with a "blind hem stitch"). The patches were attached to the inner face of the abdominal wall by 4-0 Prolene sutures. The incision was closed and the animals permitted to recover. After 24 to 34 weeks, the rabbits were sacrificed and examined.

Postoperative adhesions between the Marlex® mesh and the intestine were observed. No intestinal adhesions were observed with the composite prosthesis. The composite was observed to be completely anchored to the abdominal wall and infiltrated by host tissue.

In the rat study, mesh samples were placed between the liver and the inner peritoneal wall. The peritoneum, abdominal rectus muscle and skin were sutured closed with Ethicon 2-0 silk. The rats were sacrificed after six days and the implantation site exposed. An Instron test machine, Model 1123, was used to pull the implanted prostheses from the exposed site at a constant speed of 5 mm/min. The relative tensile force required to withdraw the prosthesis from the implant site is believed to correlate to the severity of postoperative adhesions. The test indicated that almost double the relative tensile force was required to extract the Marlex mesh implant than was required to remove the composite prosthesis.

The present invention therefore provides a prosthetic implant, amongst which are certain of the following advantages. The composite prosthesis combines the strength of a mesh material and the low adhesion incidence of a physical barrier. The composite may be anchored in place by tissue ingrowth through the mesh interstices. The specific pattern of attachment (adhesive, molding, stitching, etc.) of the mesh fabric and barrier provides a dimensionally strong implant without detrimentally affecting tissue infiltration.

The composite of the present invention is particularly indicated for repair of ventral hernias (incisional and umbilical) and chest wall defects where it is more common for the prosthetic mesh to be exposed to the abdominal viscera due to insufficient or unavailable autogenous tissue. The non-inflammatory silicone elastomer barrier prevents the mesh fabric from contacting the abdominal viscera, reducing the incidence of intestinal adhesion and fistulization. It also is contemplated that the composite prosthesis would be indicated for use in laparoscopic procedures, particularly intraperitoneal applications where the peritoneum would not be available to provide a natural barrier between the implant and the intestine.

It should be understood that the foregoing description of the invention is intended merely to be illustrative thereof and that other equivalents, embodiments and modifications of the invention may be apparent to those skilled in the art.

We claim:

1. A method for limiting the incidence of postoperative adhesions arising from a repair of an opening in a tissue or muscle wall, wherein the opening is located near a region of potential postoperative adhesion, comprising:

providing a composite prosthesis including an implantable material constructed and arranged to occlude the opening and having a plurality of interstices constructed and arranged to allow tissue ingrowth, and a barrier which does not substantially stimulate the formation of postoperative adhesions, the barrier covering the implantable material, whereby the composite prosthesis is securable in place by growth of neighboring tissue into the implantable material; and positioning the composite prosthesis for limiting the formation of postoperative adhesions with the implantable material filling or covering, thereby occluding, the tissue or muscle wall opening, and with the barrier facing away from the tissue or muscle wall opening and extending between the region of potential postoperative adhesion and the implantable material.

2. The method recited in claim 1 wherein the implantable material stimulates an inflammatory reaction when implanted in tissue.

3. The method recited in claim 1 wherein said positioning step includes positioning the composite prosthesis with the implantable material extending across the opening to the tissue or muscle wall.

4. The method recited in claim 1 wherein the repair is a chest wall reconstruction.

5. The method recited in claim 1 wherein the repair is a ventral hernia repair.

\* \* \* \* \*